United States Patent [19]

Shaulov et al.

[11] Patent Number: 5,283,524
[45] Date of Patent: * Feb. 1, 1994

[54] AC MAGNETIC SUSCEPTOMETER WITH ODD HARMONIC MEASUREMENT FOR ANALYZING SUPERCONDUCTIVE MAGNETIC MATERIALS

[75] Inventors: Avner A. Shaulov, Jerusalem, Israel; Rameshwar N. Bhargava, Ossining; Donald R. Dorman, Tarrytown, both of N.Y.

[73] Assignee: U.S. Philips Corporation, New York, N.Y.

[ * ] Notice: The portion of the term of this patent subsequent to Jan. 18, 2011 has been disclaimed.

[21] Appl. No.: 795,296

[22] Filed: Nov. 19, 1991

Related U.S. Application Data

[63] Continuation of Ser. No. 416,286, Oct. 2, 1989, abandoned.

[51] Int. Cl.⁵ .............. G01R 33/12; G01R 33/16; G01N 27/72; H01L 39/00
[52] U.S. Cl. .................... 324/239; 324/201; 324/224; 324/232; 324/233; 505/726; 505/843
[58] Field of Search ............ 324/201, 222, 224, 232, 324/233, 234, 239; 505/726, 727, 843

[56] References Cited

U.S. PATENT DOCUMENTS

| | | | |
|---|---|---|---|
| 3,651,397 | 3/1972 | Bodenheimer et al. | 324/201 |
| 3,736,500 | 5/1973 | Berkowitz et al. | 324/201 X |
| 4,105,971 | 8/1978 | Nevalainen | 324/224 X |
| 4,649,495 | 3/1987 | Cagan et al. | 324/224 X |
| 5,004,726 | 4/1991 | Shaulov et al. | 324/239 X |

FOREIGN PATENT DOCUMENTS

| | | | |
|---|---|---|---|
| 2312777 | 5/1975 | France | 324/234 |
| 0590654 | 1/1978 | U.S.S.R. | 324/234 |
| 0877416 | 10/1981 | U.S.S.R. | 324/224 |

OTHER PUBLICATIONS

Ishida et al; Superconducting transition of multiconnected Josephson network; J. Appl. Phys., vol. 52, No. 11, Nov. 1981, pp. 6798-6805.

*Primary Examiner*—Gerard R. Strecker
*Attorney, Agent, or Firm*—William L. Botjer

[57] ABSTRACT

An improved AC susceptometer and methodology for its use which is particularly suitable for the characterization of the properties of superconducting materials. Added to the circuitry of a conventional AC susceptometer is frequency domain analytical equipment for measuring the induced magnetic response. The addition of frequency domain measuring equipment permits the determination of the harmonic components of the induced magnetic response. The measurement of the harmonic components of the response also provides novel methodology for studying the phenomena of flux penetration, flux pinning and movement and permits the measurement of parameters such as lower critical field, critical temperatures, and the irreversibility line.

4 Claims, 8 Drawing Sheets

AC MAGNETIC SUSCEPTOMETER WITH ODD HARMONIC MEASUREMENT FOR ANALYZING SUPERCONDUCTIVE MAGNETIC MATERIALS

This is a continuation of application Ser. No. 07/416,286 filed Oct. 2, 1989, now abandoned.

BACKGROUND OF THE INVENTION

This application is directed to an improved AC susceptometer for measuring the properties of magnetic materials. This application is also directed to methodology for measuring the magnetic properties of materials.

Figure 1:
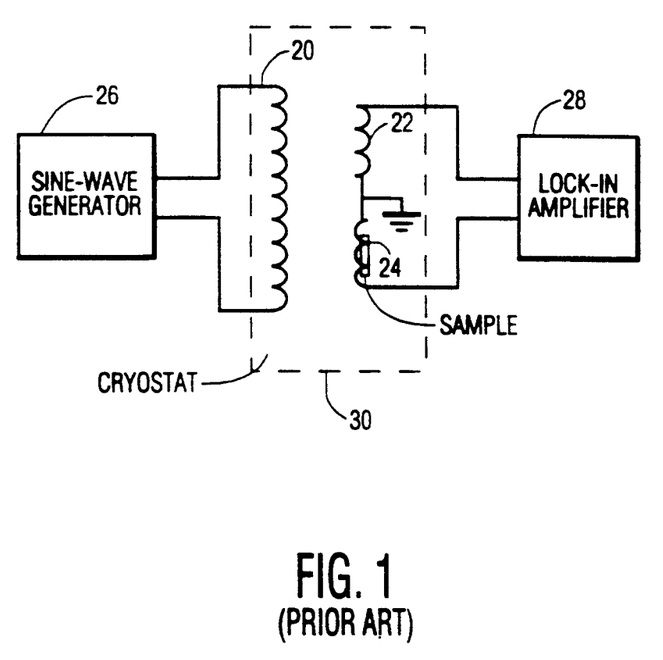
FIG. 1 is a schematic diagram of the conventional AC susceptometer utilized to measure the magnetic response of materials.

AC susceptometers are widely used in measuring magnetic properties of magnetic materials in general and of superconducting materials in particular. The basic circuit of these systems is described in FIG. 1. It consists of a primary coil 20 coaxial with a pair of balanced coils 22,24, one of which, 24 contains the sample to be measured. A sinusoidal magnetic filed of a given frequency is created by the current output of an oscillator 26 energizing primary coil 20. This alternating field induces oscillations in the magnetization of the material, and as a result an off-balance voltage is induced in the coil pair. The material's response is measured by monitoring this signal at the driving frequency using a two-phase lock-in amplifier 28. The in-phase and the $\pi/2$ out-of-phase signals are used to derive the real part ($\chi'$) and imaginary part ($\chi''$) of the magnetic susceptibility of the material. In the case of materials such as superconductors, required to be maintained at a certain temperature, a cryostat 30 surrounds the coils 20, 22, 24.

This measurement technique is well suited for the characterization of material with a linear magnetic behavior, i.e., materials in which a pure sinusoidal field induces pure sinusoidal oscillations in the magnetization at the same frequency. However, under certain temperature and bias field conditions, materials can exhibit a nonlinear magnetic behavior; namely, a pure sinusoidal field can induce nonsinusoidal oscillations in the magnetization. Thus a nonsinusoidal voltage is induced across the sample coil and components of the voltage at harmonics of the driving frequency are generated. Conventional AC susceptometers measure the response of the material at the driving frequency, ignoring the harmonic components of the response.

In a previous application, of which we are coinventors entitled "Non-Contact Test of Materials for Superconductivity" Ser. No. 380,162 now U.S. Pat. No. 5,004,726, filed Jul. 14, 1989 a simple device for detecting superconductive transitions was described.

SUMMARY OF THE INVENTION

In this application we describe an improved system which measures the alternating magnetic response of the sample material at the driving frequency as well as at harmonics of this frequency. New techniques for measuring the properties of magnetic materials are also disclosed. This improved system enables the characterization of nonlinear magnetic properties of materials. In the special case of superconducting materials, the new system provides a tool for studying the phenomena of flux penetration, flux pinning and movement in these materials. Specifically, it enables the measurements of additional parameters of practical and fundamental importance such as the lower critical field and the irreversibility line.

The known AC susceptometers are improved by the addition of frequency domain analysis of the output signal. Frequency domain analysis of the harmonics, as well as the fundamental frequency, permits measurements which were either not possible or difficult with time domain analysis. Additionally, the improved AC susceptometer permits analytical methodology which is distinct from that previously utilized.

BRIEF DESCRIPTION OF THE DRAWINGS

For a better understanding of the invention, reference is made to the following drawings, which are to be taken in conjunction with the detailed specification to follow, in which.

DETAILED DESCRIPTION OF THE DRAWING

Figure 2:
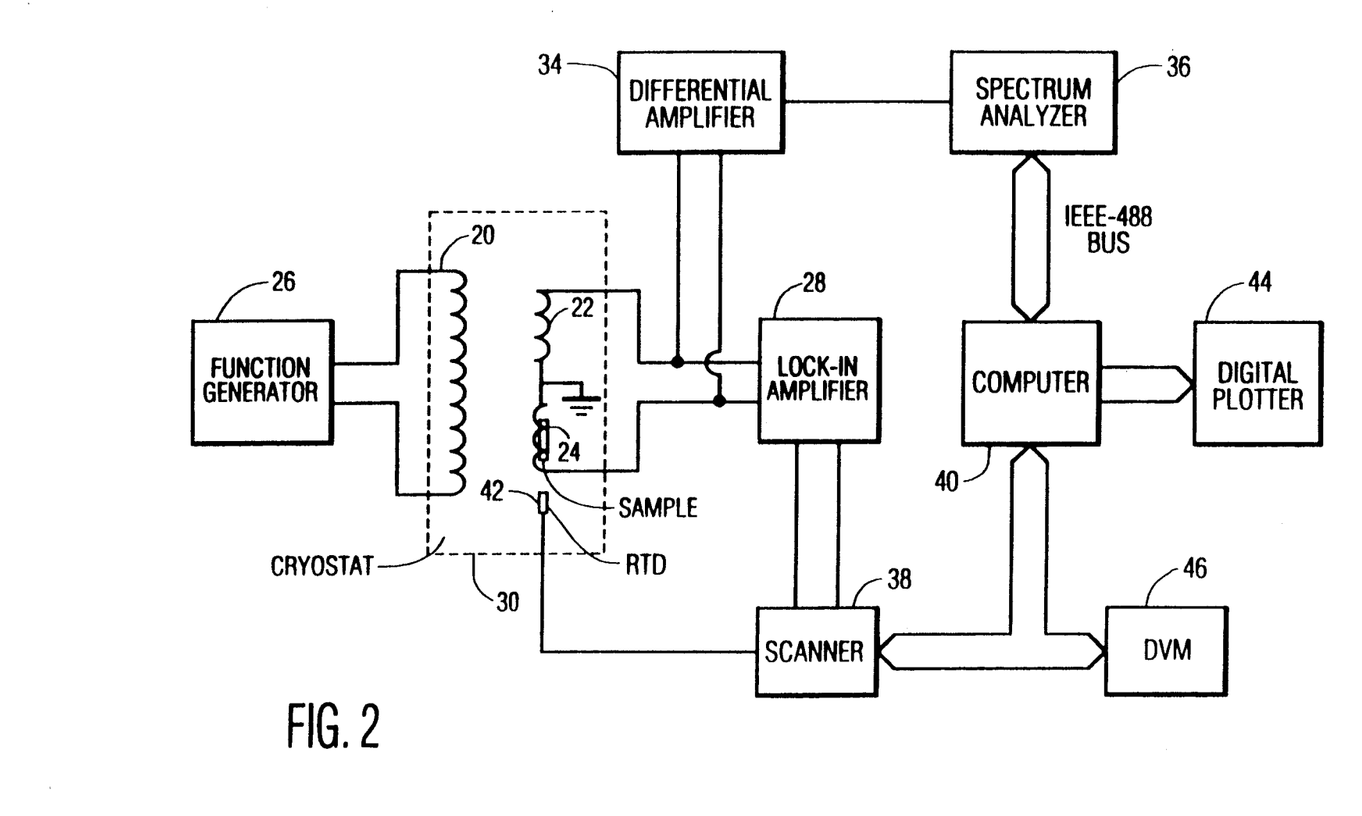
FIG. 2 is a schematic diagram of the improved AC susceptometer which permits improved analytical methodology.

A block diagram of the improved system is shown in FIG. 2. The coil system 20, 22, 24 is the same as in the conventional AC susceptometer, as described above with respect to FIG. 1. The output of the balanced pick-up coils 22, 24 is provided to a lock-in amplifier 28 that measures the phase content of the difference signal at the driving frequency. A second output is provided to a spectrum analyzer 36 through an amplifier 34 to allow frequency domain measurement of the harmonics of the output signal. A scanner 38, temperature sensor 42 and a computer 40 are included in the system to permit simultaneous measurement of the in-phase and out-of-phase signals as well as the amplitude of the harmonic components as a function of temperature and external bias fields. Optionally a plotter 44 and a digital voltmeter 46 may be included in the system to facilitate data measurement and display. An IEEE-488 bus is a preferable means of connecting the various components in order to enable computer 40 to sequence and control the various measurements. This system is distinguished from the conventional systems by its ability to measure the frequency spectrum of the magnetic response of materials to alternating fields. The following examples show the usefulness of such measurements in the characterization of superconducting materials.

A) DETERMINATION OF SUPERCONDUCTING TRANSITIONS

Figure 3:
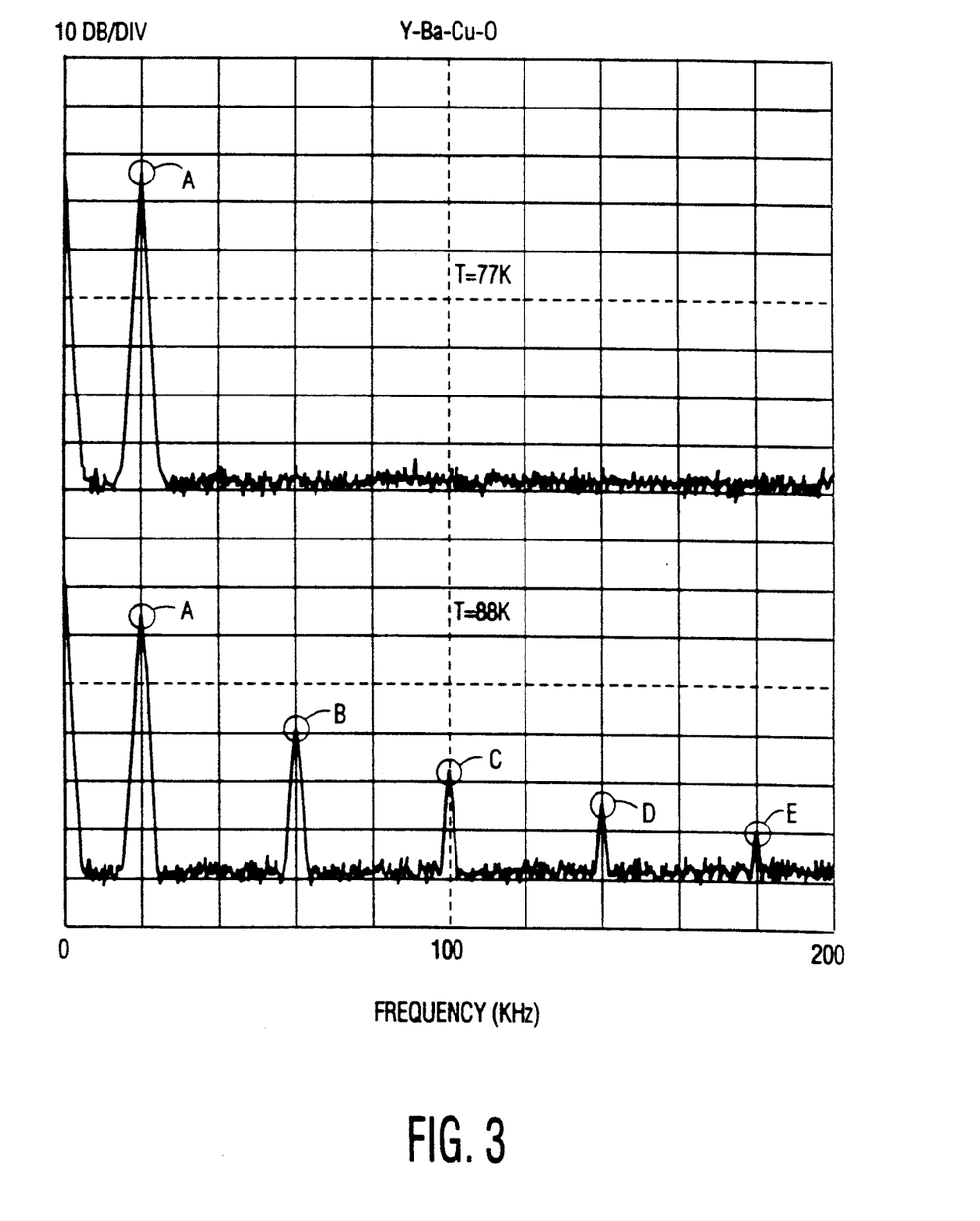
FIG. 3 is a frequency domain plot of the fundamental and harmonics of the output signal from the AC susceptometer for a sample of superconducting material at temperatures below and in the vicinity of its critical temperature.
Figure 4:
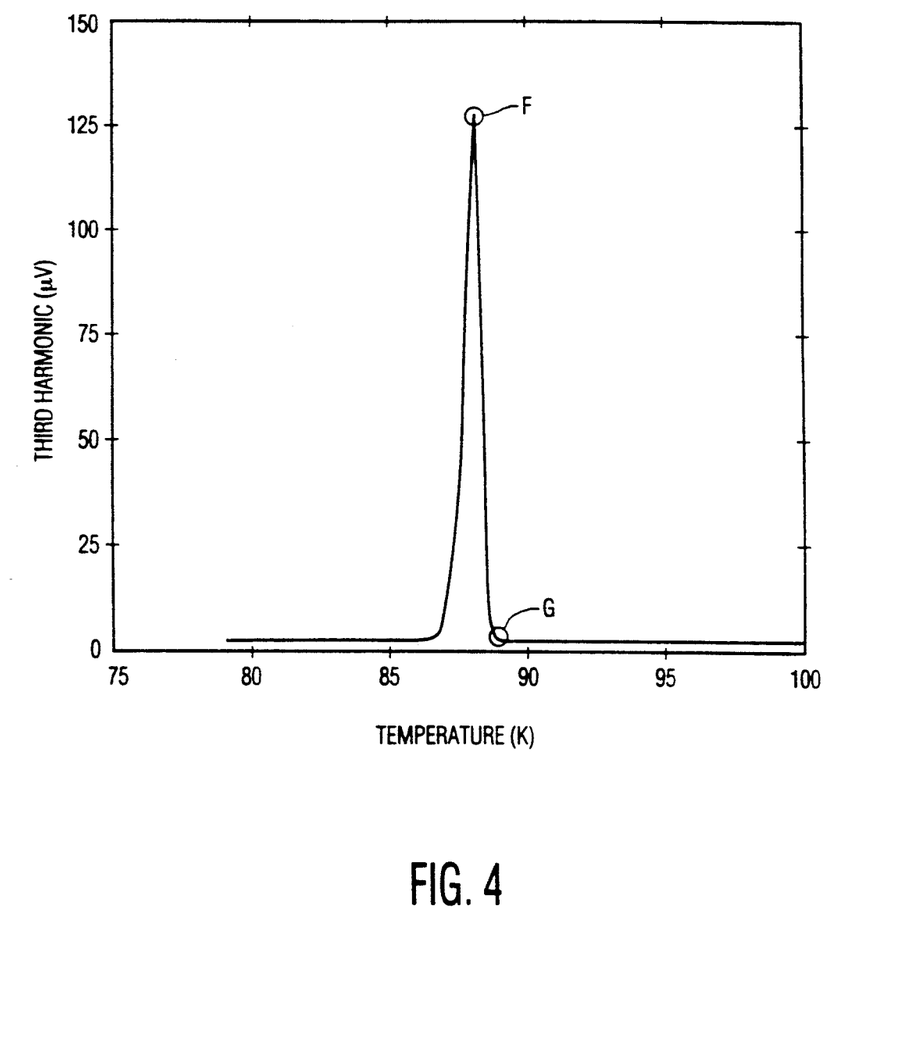
FIG. 4 is a plot of the third harmonic signal versus temperature of a sample of superconducting material cooled below its transition point.

Type II superconductors exhibit a nonlinear magnetic behavior in a close vicinity of the transition temperature, $T_c$. Above the transition temperature, and far below this point, the magnetic behavior is linear. Thus, the superconducting transition is accompanied by the generation of harmonic components in the spectrum of the material's response to a sinusoidal field. This phenomenon is demonstrated in FIG. 3. The traces in this figure show the power spectra of the magnetic response of a sintered Y-Ba-Cu-O superconductor ($T_c \approx 89K$.) to a sinusoidal field of amplitude 0.04 Oe and frequency 20 kHz. The upper trace describes the spectrum of the response at 77K. It shows only the fundamental component (point A of the upper plot) at the driving frequency (20 kHz), indicating a linear magnetic response. The lower trace in FIG. 3 describes the spectrum at 88K. This spectrum contains additional components (points B, C, D and E) at odd harmonics (third, fifth, seventh and ninth) of the driving frequency, indicating a nonlinear magnetic behavior. Measurement of the amplitude of the third harmonic component as a function of temperature (see FIG. 4) shows a peak (point F) near the transition temperature. However transition temperature is more accurately determined by the onset (point G) of the third harmonic signal as the material transforms into the superconducting phase.

Figure 5:
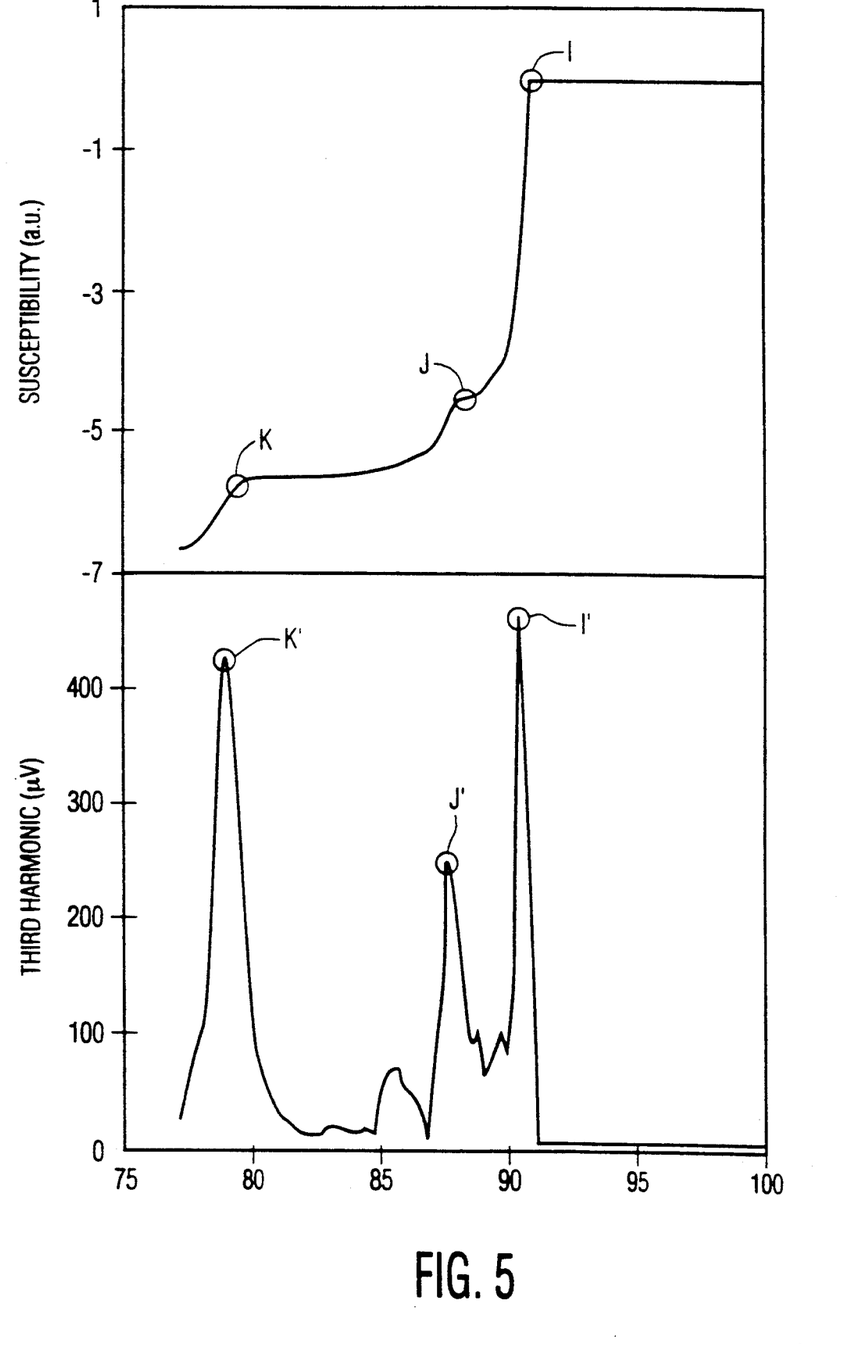
FIG. 5 is, on the bottom, a plot of the third harmonic signal of a multiphase sample of superconducting material with, on the top, a plot of its magnetic susceptibility.

FIG. 5 describes the magnetic behavior of a multiphase sample (i.e. a sample that has both non-superconducting and superconducting regions). The upper curve describes the temperature dependence of magnetic susceptibility which indicates a transition near 91K (point I). However, a close examination of this data reveals traces of additional transitions near 79K (point K) and 87K (point J). These transitions are clearly demonstrated in the measurement of the third harmonic signal as large peaks (lower curve of FIG. 5 points I', J', K'). Thus, frequency domain analysis greatly improves the determination of the multiple superconducting transistions in multiphase samples.

B) MEASUREMENT OF THE LOWER CRITICAL FIELD

Figure 6:
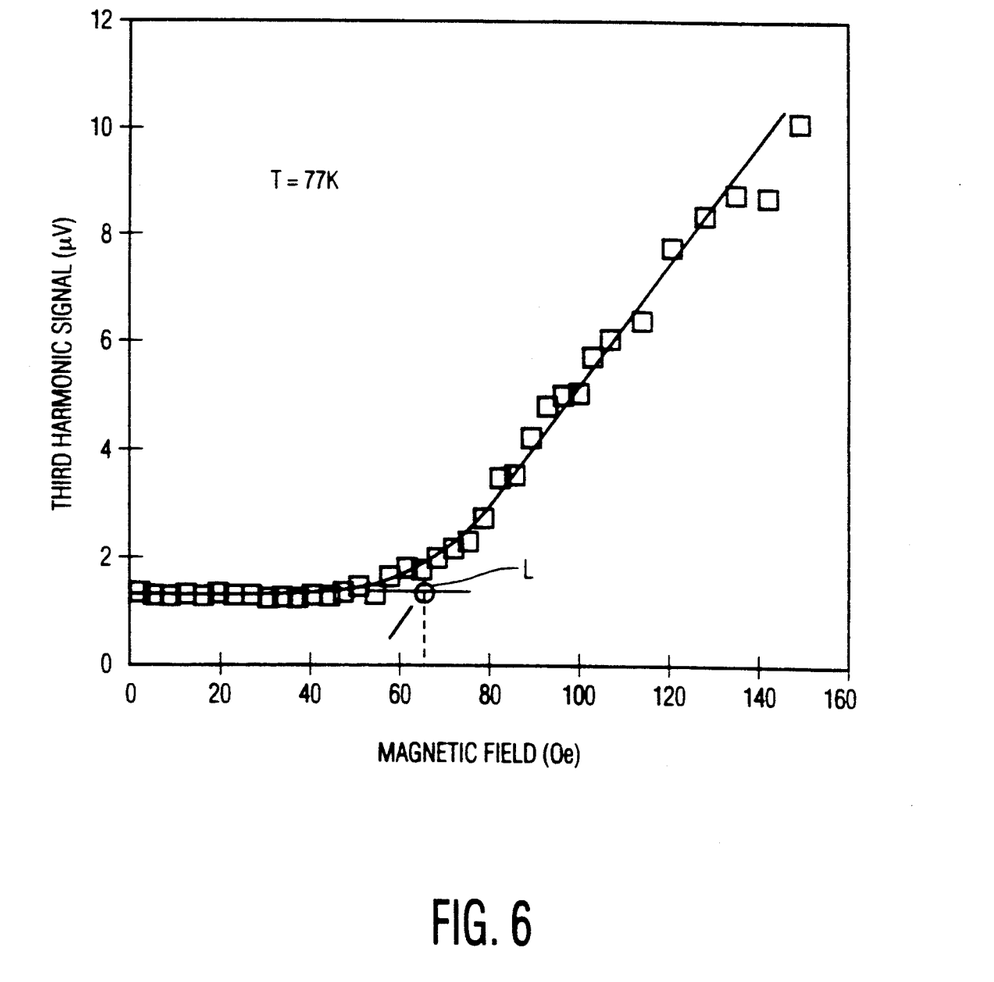
FIG. 6 is a plot of third harmonic signal versus magnetic field strength, illustrating the methodology utilized to calculate lower critical field.

The lower critical field, $H_{c1}$ is usually determined from DC measurements of the magnetization curve. The onset of nonlinear behavior in the magnetization versus field curve is identified as $H_{c1}$. The accuracy of this method is limited because of the difficulty in detecting relatively small deviations from linearity just above $H_{c1}$. Measurements of harmonic components in the alternating magnetic response provides a new tool for more accurate determination of $H_{c1}$. In order to probe $H_{c1}$, at a given temperature, a sinusoidal field is superimposed on a colinear steady bias field. As the steady bias field is incrementally raised, the onset of nonlinear behavior of the magnetization at $H_{c1}$ is indicated by the appearance of harmonic components in the response. This is illustrated in FIG. 6 which describes a measurement of the amplitude of the third harmonic signal as a function of the bias field in a sintered sample of Y-Ba-Cu-O at 77K. The third harmonic signal remains below the background noise level as the bias field is increased from 0 up to about 60 Oe, and rises abruptly thereafter. The critical field $H_{c1}$ can be determined by extrapolating the roughly linear rise of the third harmonic signal downward to a zero noise level. As is shown in FIG. 6 if one extends the linear portions of each component of the line the extensions cross at point L. The lower critical field $H_{C1}$ is thus seen to be located at 64 oersteds.

C) MEASUREMENT OF THE IRREVERSIBILITY LINE

The temperature dependence of the lower and upper critical fields, $H_{c1}$ and $H_{c2}$, describe two lines in the field-temperature plane. Below the $H_{c1}$-line the material is in a superconducting state, i.e. magnetic flux is completely excluded from the interior of the material. Above this line and below the $H_{c2}$-line the material is in a mixed state. In this state, flux penetrates the material in a form of small flux tubes parallel to the field. The core of each tube is normal (nonsuperconducting), but the material surrounding each flux tube remains superconducting. Above the $H_{c2}$-line the material is in the normal state.

Recently, a new line was disclosed in the region between the $H_{c1}$ and $H_{c2}$ lines. This so called "irreversibility" line describes a line below which irreversibility in the magnetization sets in as a result of flux pinning. Above this line, thermal activation permits unpinning of flux lines within the time scale of the experiment.

It is practically important to determine the irreversibility line because high critical current density can be expected only below this line. Using the improved AC susceptometer, one can determine the irreversibility line by measuring the temperature dependence of the harmonic components under steady bias fields. The transition from a nonlinear, irreversible behavior of the magnetization below the irreversibility line to a linear, reversible behavior above this line is indicated by disappearance of the harmonic components.

Figure 7:
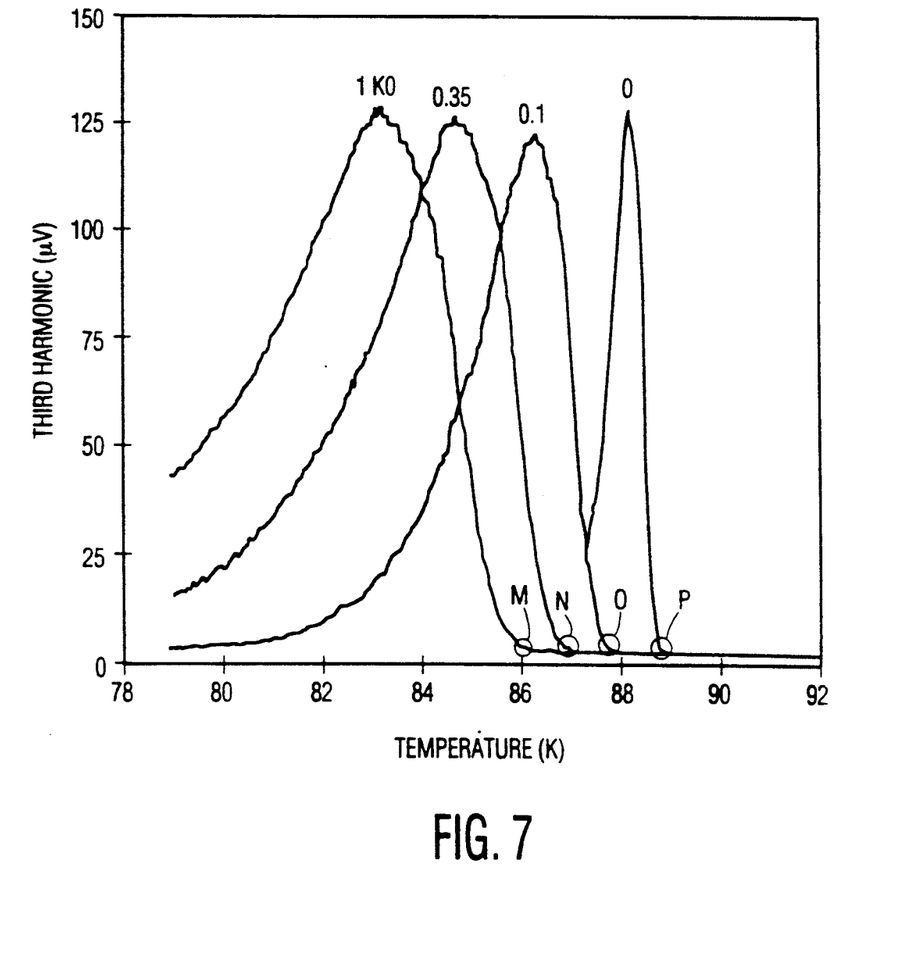
FIG. 7 is a third harmonic signal versus temperature plot of a sample of superconducting material at various magnetic field strengths utilized in the calculation of the irreversibility line.
Figure 8:
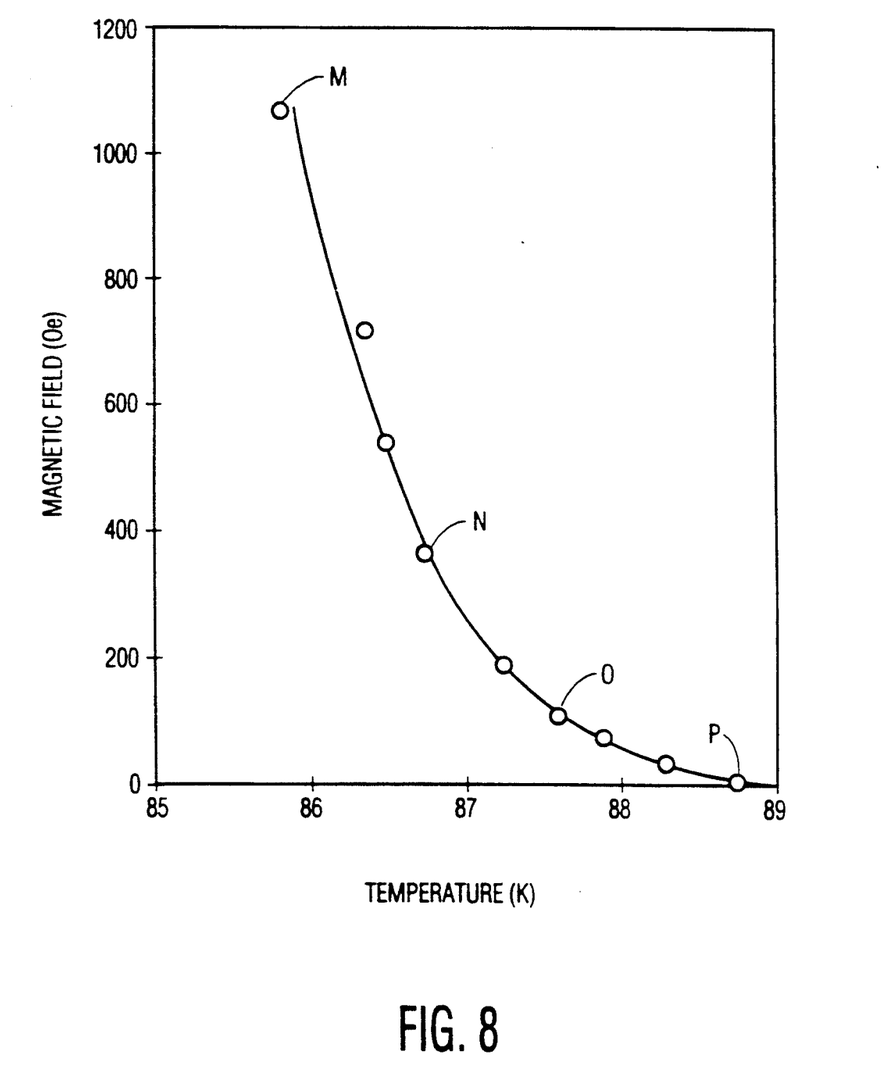
FIG. 8 is a temperature versus magnetic field strength graph showing the irreversibility line plotted thereon.

FIG. 7 shows the results of measurements performed on a sintered Y-Ba-Cu-0 sample at a number of magnetic field strengths. It is seen that the third harmonic signal exhibits a sharp drop to the noise level at well defined temperatures. See points M, N, 0, P on FIG. 7. These temperatures shift down as the bias field increases. In FIG. 8 points M, N, O, P are plotted as a function of temperature versus magnetic field. Measurement of these transition temperatures for different bias fields yields the irreversibility line as shown in FIG. 8 which is interpolated through the plotted points.

The above examples show that the upgraded AC susceptometer, which includes provision for measuring the harmonic components of the alternating magnetic response, provides unique capabilities in characterization of superconducting materials. Specifically, this system is distinguished from conventional susceptometers by its ability to measure nonlinear magnetic properties. Although the present disclosure refers the system described in FIG. 2, it is understood that modifications may be resorted to without departing from the basic concept of the invention. For example, the spectrum analyzer in FIG. 2 may be replaced by a low cost circuit for detection of the harmonic signals. Such modifications are considered to be within the scope of the invention.

What is claimed is:

1. A apparatus for measurement of lower critical field of a sample of cooled superconductive material, comprising:
    means for applying a magnetic bias field to the sample of material;
    means for superimposing a sinusoidally varying field on said bias field;

means for altering the strength of the bias field;

means for measuring the amplitude of the odd numbered harmonic component of the induced magnetic field in the sample;

means for graphically displaying the amplitude of the odd numbered harmonic component as a function of bias field strength, said amplitude generally appearing constant at lower field strengths, which represents background noise, and a sloped line rising at a certain amplitude; and means for determining the lower critical field by interpolating the sloped line of the amplitude of the odd numbered harmonic component with the background noise level.

2. The apparatus as claimed in claim 1 wherein the odd numbered harmonic component comprises the third harmonic.

3. Apparatus for determining the irreversibility line of a sample of cooled superconductive material comprising:

means for applying a number of different bias fields to said sample of material;

means for measuring the amplitude of an odd numbered harmonic component of the magnetic field induced in the sample of material;

means for displaying graphically the amplitude of the odd numbered harmonic component versus temperature at the different bias field strengths;

means for determining the temperature at which the odd numbered harmonic component exhibits a sharp drop to the noise level for each of the bias field strengths; and means for plotting the temperatures at which the bias fields drop to the noise level as a function of magnetic field strength, the line interpolated through these temperatures providing the irreversibility line.

4. The method as claimed in the claim 3 wherein the odd numbered harmonic component is the third harmonic.

* * * * *